United States Patent
Kehr et al.

(10) Patent No.: US 6,398,723 B1
(45) Date of Patent: Jun. 4, 2002

(54) ENDOSCOPE HAVING AN IMMOBILIZATION SYSTEM FOR COMPONENTS OF AN INNER OPTICAL SYSTEM

(75) Inventors: Ulrich Kehr, Ostfildern; Jürgen Rudischhauser, Tuttlingen, both of (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/492,051

(22) Filed: Jan. 26, 2000

Related U.S. Application Data (63) Continuation of application No. PCT/EP98/04813, filed on Jul. 31, 1998.

(30) Foreign Application Priority Data

Jul. 31, 1997 (DE) .......................................... 197 32 991

(51) Int. Cl.[7] ................................................. G02B 7/02
(52) U.S. Cl. ...................... 600/160; 600/161; 359/819; 359/503; 359/808; 359/435
(58) Field of Search ................................. 600/160, 138, 600/161; 359/434, 435, 808, 811, 819, 503

(56) References Cited

U.S. PATENT DOCUMENTS

| | | | |
|---|---|---|---|
| 4,148,550 A | 4/1979 | MacAnally | 350/54 |
| 4,750,476 A * | 6/1988 | Forkner et al. | 128/6 |
| 5,419,313 A * | 5/1995 | Lemke | 128/6 |
| 6,201,649 B1 * | 3/2001 | Rudischhauser et al. | 359/808 |

FOREIGN PATENT DOCUMENTS

| | | |
|---|---|---|
| DE | 3431631 C2 | 10/1990 |
| DE | 3912720 C2 | 8/1992 |
| DE | G9318440.9 | 4/1994 |
| DE | 19732991 C2 | 9/1999 |
| EP | 0 292 602 A1 | 11/1988 |
| EP | 0 260 855 A2 | 12/1988 |
| WO | WO90/04350 | 10/1989 |

* cited by examiner

*Primary Examiner*—John P. Leubecker
*Assistant Examiner*—Jocelyn Ram
(74) *Attorney, Agent, or Firm*—St. Onge Steward Johnston & Reens LLC (57) ABSTRACT

An endoscope has a tubular shaft in whose interior is arranged at least one component of an optical system. At least one support element made from a shrinkable material surrounds at least partially said component in a radial gap between the outer side of said component and the inner side of said tubular shaft. After shrinking of said support element the radial gap is filled up in a manner such that the component is immobilized on the inner side of the tubular shaft via the shrunken support element (FIG. 1).

15 Claims, 5 Drawing Sheets

ENDOSCOPE HAVING AN IMMOBILIZATION SYSTEM FOR COMPONENTS OF AN INNER OPTICAL SYSTEM

CROSS REFERENCE OF PENDING APPLICATION

This application is a continuation of pending international application PCT/EP 98/04813 filed on Jul. 31, 1998.

BACKGROUND OF THE INVENTION

The present invention relates to an endoscope having a tubular shaft in whose interior is arranged at least one component, in particular lenses, aperture stops, filters, of an optical system, at least one support element that at least partially surrounds the component being provided between the outer side of the component and the inner side of the tubular shaft.

An endoscope of this kind is known from U.S. Pat. No. 4,148,550.

Endoscopes are used generally in surgery to inspect body cavities and hollow organs. Endoscopes have an elongated tubular shaft in which components of an optical observation system are arranged. Further apparatuses, usually a light delivery apparatus, and optionally ducts for instruments, flushing fluid, or the like, are often provided in the interior of the endoscope shaft. Light delivery is usually accomplished via light-guiding optical fibers.

In this case the optical system is received in a separate inner tube in the endoscope shaft.

Endoscopes can be of rigid or flexible configuration, the endoscope shaft correspondingly being manufactured from metal or a flexible plastic material.

The optical systems provided in endoscopes are constructed from components arranged along the tubular shaft axis, such as lenses (in particular rod lenses of the so-called Hopkins optical system), aperture stops, filters, and the like, and their purpose is to reproduce an image of as large a field of view as possible with high resolution and high contrast. The most important prerequisite for this is precise arrangement of the components of the optical system in the tubular shaft of the endoscope. The relative positions of the components of the optical system are not variable but rather are precisely defined, since any shift in the components relative to one another results in decreased image sharpness and resolution.

The components therefore must be precisely immobilized in the tubular shaft of the endoscope so as to remain there immovably.

The components of an optical system are usually slid into the tubular shaft of the endoscope, spaced apart from one another with spacers, and immobilized using end-located terminating elements. This type of immobilization system is insufficient, however, since tolerances can result in radial movement back and forth. A thin air gap is present between the outer side of the components and the inner side of the tubular shaft, or the components rest by way of their outer sides against the inner side of the tubular shaft.

In addition, and most importantly, the lenses of the optical system, made of glass material, can break during handling of the endoscope, for example if the endoscope is dropped or set down too firmly onto a hard surface, since because of the very thin air gap between component and tubular shaft, even slight flexing of the tubular shaft can cause forces or torques to act on the components and result in the breakage of lenses.

This problem has been tackled, for example in the case of rod lenses, by way of a "dog-bone" shape for the lens, i.e. a shape in which the ends of the rod lens have enlargements, called rim cylinders. A conforming fit with the tubular shaft is then present only in the region of the rim cylinders, and the remaining periphery of the rod lens is separated from the tubular shaft by a gap.

During cleaning, shocks occur (due to ultrasound, dishwasher, etc.) that cause the lenses to strike against the inner tube as a result of their radial clearance. Impacts also occur between the lens and spacing element (due to wear, contamination, etc.).

One solution to the problem of joining the lenses of an optical system in an endoscope to one another is described in the aforesaid U.S. Pat. No. 4,148,550.

The endoscope described therein has an outer protective tube on whose inner side a layer with light-transmitting fibers is provided, and an inner tube in which a number of rod lenses, which form an optical system, are arranged axially one behind another.

As already mentioned, it is necessary for the operation of the optical system for the rod lenses to be arranged at a defined axial spacing from one another in the inner tube of the endoscope. Spacers in the form of spacer tubes, usually made of metal, are used for this purpose in the existing art.

In U.S. Pat. No. 4,148,550, the join between the rod lenses is created using sleeve-shaped elements which enclose the lens ends of at least two adjacent lenses.

These elements are made of a flexible sleeve-shaped material and have longitudinally extending slots that are provided for the introduction of a tool and the passage of cleaning gases or liquids for the lenses. In addition to holding together the rod lenses that are arranged one behind another, the elements also serve to allow the flexible endoscope to bend while preventing breakage of the rod lenses. These elements themselves can provide bracing with respect to the inner wall of the tubular shaft, but additional annular support elements can also be provided.

Attachment or immobilization of the rod lenses, joined by way of the support elements, in the inner tube of the endoscope is accomplished by press-fitting, specifically by the fact that, for example, a slightly oval or triangular cross section is imparted to the inner, initially cylindrical tube enclosing the rod lens system, so that the rod lenses, with their round cross section, are firmly press-fitted. It is further proposed to use suitable adhesives.

The elements provided in this U.S. Pat. No. document provide for the rod lenses to be joined to one another, and provide for bracing against the parts of the endoscope that surround them. The axially nondisplaceable join must be effected separately, since otherwise the lens arrangement as a whole can move axially back and forth in the interior of the endoscope, which is undesirable due to the adverse effect on optical quality and the risk of breakage of lens elements.

DE 19 12 720 C2 discloses an endoscope whose tubular shaft is made of a transparent and optically clear plastic material into which the optical elements of the objective and the lens system are placed. This hollow cylinder serves as a light guide in order to guide illumination light from the proximal to the distal end of the endoscope.

In order to shield the lenses present in the hollow cylinder from the entry of light from the light guiding system, a light-absorbing and/or reflective element is provided between the hollow cylinder and the objective or the lens system. This element can be configured as a plastic heat-shrink sleeve. The lenses of the lens system and the objective are first placed into this plastic heat-shrink sleeve and positioned in the correct position; then the heat-shrink sleeve is shrunk by the application of heat so that it holds the lenses. This assemblage is then slid into the tubular shaft. The purpose of the plastic heat-shrink sleeve is thus to hold the lenses in a specific orientation with respect to one another, and furthermore to serve as a light-absorbing or light-reflecting element.

DE 33 31 631 C2 has disclosed a lens retaining system for radial adjustment of rod lenses in an optical tube in the region of the lens ends, in which annular retaining means are provided which hold the lenses at a radial distance from the inner surface of the tube.

Against this background, it is the object of the present invention to create an endoscope of the kind cited initially in which the components of the optical system are immobilized as simply as possible but nevertheless securely in the interior of the tubular shaft, and also can be protected against the action of external forces or torques.

SUMMARY OF THE INVENTION

This object is achieved, in an endoscope, in that the support element is manufactured from a shrinkable material, and that the component is immobilized on the inner side of the tubular shaft by way of the support element shrunken in the tubular shaft.

A "shrinkable material" for purposes of the present invention is understood to mean on the one hand a cold-stretched thermo-plastic material that contracts back to its original state when heat-treated. The shrinkage effect is based on the effort by the plastic molecules to return to their original, strain-free arrangement. This is also referred to as "memory" capability or "elastic shape memory." Examples of shrinkable materials are PETP, PE, or PVC.

On the other hand, a "shrinkable material" is also understood to mean a metal alloy or a plastic material with a memory effect that has at least two states, one state being achieved via shrinkage of the material. In materials of interest for the invention, the memory effect must be abolished after shrinkage.

This type of immobilization using shrinkable support elements is extremely simple, since the component can first be introduced in accurately fitted fashion into the tubular shaft, along with the support element in its unshrunken, stretched state, and positioned appropriately. As a result of heat treatment, the material shrinks (i.e. contracts) and is pressed into the gap between the outer side of the component and the inner side of the tubular shaft. Depending on the configuration of the support elements, it is possible in this context to use materials that shrink in the direction of the tubular shaft axis and/or that shrink in the transverse direction. What is critical is that the shrinking material fill up the gap between component and tubular shaft in such a way that the component is immobilized, by way of the shrunken support element, on the inner side of the tubular shaft. The heated support element thus adapts both to the external shape of the component and to the internal shape of the tubular shaft, regardless of their individual configurations. After cooling, the shrunken material fills up the air gap between the outer side of the component and inner side of the tubular shaft over certain axial and peripheral regions in the radial direction. Because the material has shrunken into this gap upon shrinking, i.e. attempted to expand radially but was limited because of the narrow gap, the shrunken material exerts an applied pressure that acts radially on both sides and ensures sufficient immobilization of the axial and radial relative position of the component and tubular shaft. Neither adhesives nor other attachment means or clamping connections are necessary, nor do the components need to be fitted exactly into the tubular shaft, since the support element, which is initially stretched and only later is present in shrunken form, ensures immobilization in this case.

The provision of a shrunken support element made of a plastic material has the further considerable advantage that it additionally constitutes protection for the components of the optical system against external forces, since it is elastic and can therefore damp impacts. Even if the endoscope were to be dropped, the risk of breakage of the components of the optical system is thus greatly reduced.

The components of the optical system can, in this context, be lenses, filters, aperture stops, objective cartridges, or any other conceivable components used in endoscope optics. Relevant lenses are rod lenses or conventional lenses; the rod lenses can be provided as smooth cylinders or in a dog-bone, barrel, or any other possible shape. The optical system usually comprises several components arranged axially one behind another, all of which, but optionally also only two adjacent ones of which, can be respectively joined to one another with a shrunken support element according to the present invention and at the same time secured in the tubular shaft.

A "tubular shaft" for purposes of the present invention is understood to mean any tubular part of an endoscope in which the optical system is arranged. This will usually be an inner tube that, together with further tubes for the light guide, flushing duct, or the like, is enclosed by an outer tube. If no further ducts are provided in the endoscope interior, however, the tubular shaft can also be the outer shaft of the endoscope. The tubular shaft of an endoscope according to the present does not need to be rigid; it can instead also be flexible, since the shrunken support element is itself flexible and therefore adapts to any bending of the tubular shaft without causing loosening of the immobilization of the component on the inner side of the tubular shaft.

The selection of the material and its shrinkage temperature is also based on the type of endoscope and its intended purpose. Endoscopes in the medical field are sterilized at approximately 140° C., so that materials with softening points above 140° C. are used. If materials with softening temperatures less than 140° C. are to be used, it is possible to provide insulation that ensures, especially with so-called flash autoclaving, that the softening temperature is not reached in the interior of the endoscope shaft. Temperatures of up to 200° C. can be tolerated by current optical cements that are used, for example, to close off the tubular shaft at the distal end with an optical window. If materials are used that shrink only at even higher temperatures (>200°–400° C.), care must be taken that only the shrinkable material is exposed to such high temperatures.

In a preferred embodiment, the support element comprises a sleeve that covers a majority of the outer side of the component.

The provision of a heat-shrink sleeve of this kind offers the advantage of achieving particularly immovable and secure immobilization of the component on the tubular shaft, since the heat-shrink sleeve, so to speak, receives the component within it, i.e. encloses it circumferentially, and thus additionally protects the components from forces on all sides.

It is understood that spacers, for example spacer tubes made of metal or plastic, can also be provided in order to ensure the defined spacings between the components of the optical system, and can then also be immobilized by way of the support element according to the present invention. Spacers of this kind can also, however, be arranged without further immobilization between the components that are immobilized via the support element.

In a further preferred embodiment, the support element comprises at least one ring.

A single ring is advantageously used to immobilize a rod lens present in dog-bone form that is additionally made nontilting in the tubular shaft by way of the rim cylinders provided in the end regions of the rod lenses. The ring is then advantageously arranged in the center region of the dog-bone-shaped rod lens. Annular support elements are moreover particularly be immobilized. The ring then surrounds and immobilizes the entire periphery of such a narrow component.

In a particularly preferred embodiment, the support element comprises two rings that are arranged at opposite ends of the component.

The advantage of this feature is that any tilting of the component inside the tubular shaft is reliably prevented by two support elements that are axially spaced apart from one another. It is also advantageous that annular support elements can be particularly easily slid onto rod lenses when the endoscope is being assembled. It is understood that in particular with elongated components, more than two rings can also be used as support elements.

In a further embodiment, the support element comprises at least one half-ring.

The advantage of this feature is that the immobilization of the component with respect to the tubular shaft according to the present invention can be brought about in a material-saving manner. It is understood that several half-rings, optionally arranged alternatingly on opposite sides of the component, can also be provided.

The fact that a component is not enclosed in completely circumferential fashion by the support element allows the axial passage of gases (e.g. for pressure equalization) or the passage of flushing liquids.

In a further preferred embodiment, the support element comprises at least two strips that extend in the longitudinal direction of the tubular shaft.

Strips of this kind ensure attachment over their entire length, so that even axially elongated components such as rod lenses can be securely immobilized, even if they are not present in a dog-bone shape, while ensuring that tilting within the tubular shaft cannot occur. It is understood that more than two strips can also be provided, the arrangement of three strips being particularly advantageous if they are distributed uniformly around the circumference of the component. A strip of this kind according to the present invention need not, of course, extend over the entire length of the component, but rather can also be substantially shorter, to the point of being "pads" of shrinkable material. Such pads can be distributed in any desired fashion on the outer side of the component.

Pressure equalization of course also occurs when strips are used.

In a further particularly preferred embodiment, the support element comprises a band wound in helical fashion.

A band of this kind wound in helical fashion protects the outer side of the component circumferentially, and additionally provides for the possibility of pressure equalization between the two axial ends of the component. This is because differences in air pressure between the two ends can result in longitudinal forces that can possibly affect the axial position of the components.

In a further preferred embodiment, the outer side of the component is smooth.

The advantage of this feature is that, for example, sleeve-shaped support elements can easily be slid onto the component.

In a further embodiment, the outer side of the component has at least one groove, and the support element is arranged in the region of the groove.

The advantage of this feature is that a particularly intimate join between the outer side of the component and the shrunken material of the support element is achieved. During the heat treatment necessary for shrinking the shrinkable material, the materials shortens while axially increasing in thickness, as already explained. The groove is thereby filled up by the support element. After cooling, the material entering the gap inhibits any axial relative displacement between support element and component.

In a further particularly preferred embodiment, the outer side of the component has at least one land, and the support element is arranged in the region of the land.

The shrunken shrinkage element surrounds the land. It is also possible to provide several lands between which the support element is arranged; in this case the component is additionally supported in the tubular shaft by way of the lands. It is understood that the shape of the land can be rectangular, pointed, or rounded, depending on the conditions of the particular component. The land, projecting into the material and surrounded by it, mechanically inhibits any relative movement between the support element and component.

In a further preferred embodiment, the inner side of the tubular shaft is smooth.

The advantage of this feature is that the assemblage of support element and component can easily be slid into the tubular shaft.

In a further embodiment, the inner side of the tubular shaft has at least one groove, and the support element is arranged in the region of the groove.

When a groove is arranged on the inner side of the tubular shaft, once again the shrinkable plastic material of the support element can expand, during the heat treatment, into the groove, fill it up, and then inhibit any axial relative movement between the tubular shaft and support element.

In an embodiment, the wall of the tubular shaft has at least one outwardly directed protrusion in the form of a spherical segment, and the support element is arranged in the region of the protrusion.

This feature offers the considerable advantage of protecting the component especially well from outside forces, since a particularly thick bead-like layer of the damping material is present between the component and the tubular shaft wall precisely in the region of the contact surface with the tubular wall, specifically above one or more protrusions.

In a further embodiment, the inner side of the tubular shaft has at least one land, and the support element is arranged in the region of the land.

In this case the land is surrounded by the support element and inhibits any axial displacement of the support element relative to the inner side of the tubular shaft.

In a preferred embodiment, several components are arranged axially in the interior of the tubular shaft along the tubular shaft axis; and the support element extends over the components and the latter are thus immobilized in an axial arrangement with respect to one another.

The considerable advantage of this embodiment is not only that the support element guarantees immobilization of the components on the inner side of the tubular shaft, but also that the individual components of the optical system, arranged axially one behind another, are also immobilized relative to one another. Thus not only it is possible to prevent any axial displacement of the individual components in the tubular shaft, but the spacing between the individual components that is necessary for correct functioning of the optical system is additionally fixed and ensured. The support element according to the present invention thus performs three functions: firstly, the components are immobilized on the inner side of the tubular shaft; secondly, the components are joined to one another and immobilized with respect to one another; and thirdly, the components are protected over their entire length from external forces, since the latter are damped by the elastic material. Any movement of the components of the optical system in the tubular shaft that might adversely affect the optical system is thus practically ruled out.

The object of the invention is furthermore achieved by a method for mounting components, in particular lenses, aperture stops, filters, of an optical system, in the interior of a tubular shaft of an endoscope, in which at least one support element that at least partially surrounds the component is brought onto the outer side of the component of the tubular shaft, and this assemblage is introduced into the tubular shaft, that is characterized in that a support element made of a shrinkable material is applied; and after introduction of the assemblage into the tubular shaft, a heat treatment is performed such that the material of the support element shrinks, thereby immobilizing the assemblage on the inner side of the tubular shaft.

This method for mounting components is particularly simple, since the support element is first brought, in its stretched initial state, onto the component outside the tubular shaft, or the components are slid into it; and only then is the assemblage introduced into the tubular shaft, sufficient radial clearance being present to easily allow such installation, since in this state the shrinkable material is only a thin film. It is only as a result of the heat treatment that is then performed that the shrinkable material increases in thickness, and creates the intimate contact between the inner side of the tubular shaft and the outer side of the component. If grooves, lands, elevations, or other elements are provided on one of the participating surfaces, these are, so to speak, "surrounded" and "filled up" by the shrinkable material that is in a rubber-like state as a result of the heat treatment.

In a preferred development of the method according to the present invention, several components are arranged axially one behind another along the tubular shaft axis, and a support element extending over the several components is applied in such a way that after the heat treatment, the components are additionally immobilized relative to one another in their axial arrangement.

The advantage of this feature is to guarantee, without additional actions, that the components are immobilized in the interior of the tubular shaft and are joined and immobilized relative to one another. The components can be lined up outside the tubular shaft and then joined together by way of the support element; this is particularly easy because visibility is not blocked by the tubular shaft. Only then is the assemblage slid into the tubular shaft.

The heat treatment and the material properties of the shrinkable material ensure that the components are arranged inside the tubular shaft in a manner protected against axial and radial displacements. Two kinds of immobilization of the components are thus achieved, namely immobilization on the tubular shaft and immobilization relative to one another.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

Further advantages and embodiments of the invention are explained below with reference to the Figures, in which:

FIG. 5b shows a longitudinal section of the support element of FIG. 5a;

FIG. 6b shows a longitudinal section of the support element of FIG. 6a;

FIG. 7b shows a longitudinal section of the arrangement of FIG. 7a;

FIG. 8b shows a partial side view of the band of FIG. 8a;

DETAILED DESCRIPTION OF PREFERRED EMBODIMENTS

Figure 1:
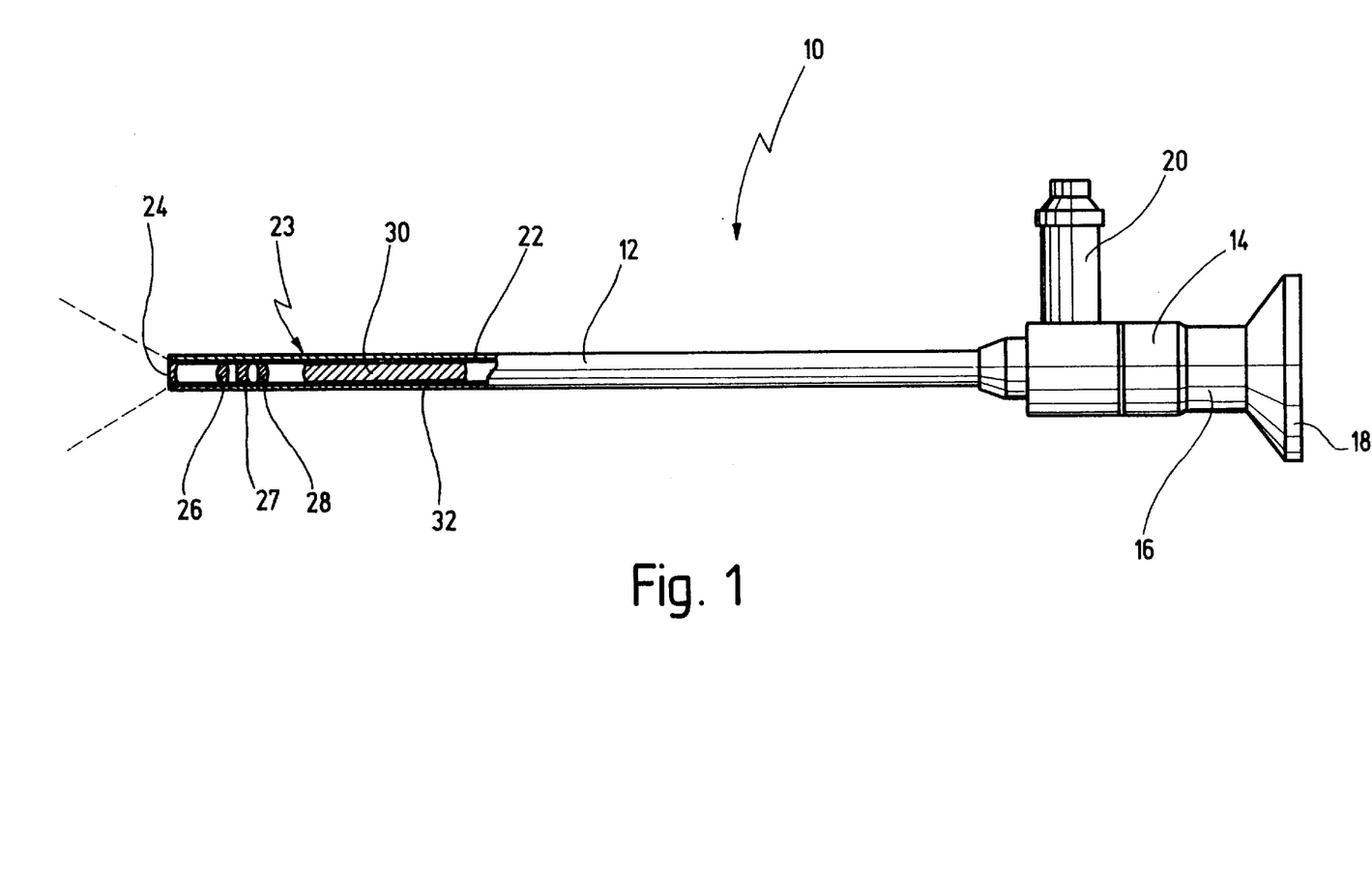
FIG. 1 shows a partially cut-away side view of an endoscope according to the present invention.
Figure 2:
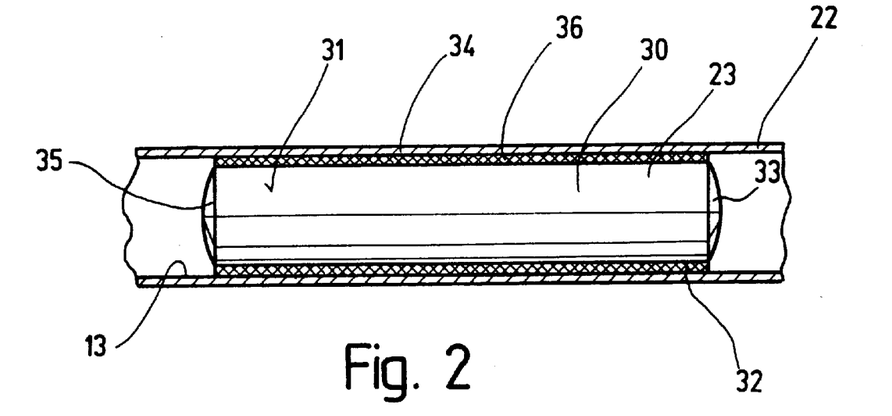
FIG. 2 shows a portion of the endoscope of FIG. 1 in a longitudinal section and in a first embodiment.

An endoscope shown in FIGS. 1 and 2 is labeled in its entirety with the reference number 10.

Endoscope 10 has an elongated tubular shaft 12 at whose proximal end a housing 14 is arranged. An eyepiece 16 with an eye-piece cup 18 is provided in the housing.

An optical system that serves to bring an image, acquired at the distal end, to the proximal end is received in endoscope 10. A light guiding system (not described further here), in the form of optical fibers that are joined to a light source (not shown here) via an extension 20 leading off laterally from housing 14, is usually arranged in tubular shaft 12. An inner tube 22 that receives numerous components 23 of the optical system is arranged in tubular shaft.

Distally, a window 24 constitutes a sealed closure of the distal end of inner tube 22, through which image information penetrates into the optical system.

Inner tube 22 contains numerous lenses 26, 27, 28, also including rod-shaped lenses as is the case, for example, in a so-called Hopkins optical system.

FIG. 2 shows a segment of inner tube 22 in which rod-shaped lens 30 is mounted. Rod lens 30 has at each of its opposing ends an optical surface 33 and 35. A support element 32 in the form of a sleeve segment 34 is slid over its smooth outer side 31.

Sleeve segment 34 consists of a sleeve film made of cold-stretched PVC.

During assembly, first of all sleeve segment 34, which is configured as a relatively thin film, is slid over rod lens 30. Then the assemblage made up of rod lens 30 and slid-on sleeve segment 34 is inserted into inner tube 22 and brought into the axial position shown in FIG. 2. A corresponding procedure can then be followed for the other components of the optical system.

The assemblage made up of inner tube, support element 32, and rod lens 30 is then subjected to a heat treatment in which the shrinkable material of sleeve segment 34 shrinks. In this shrinkage operation, the material has a tendency to contract axially and thereby to expand slightly in the radial direction. As a result, gap 36 between outer side 31 of rod lens 30 and inner side 13 of inner tube 22 is completely filled up with the softened shrinking material. This results in a contact pressure that acts radially between inner side 13 of inner tube 22 and outer side 31 of rod lens 30, so that lens 30 is immobilized in axially nondisplaceable fashion in inner tube 22. After the material has cooled it becomes relatively stiff but remains elastic, so that an elastic sheath surrounds rod lens 30. This elastic sheath then also cushions against external forces and thus greatly reduces the risk of breakage of rod lens 30.

Figure 3:
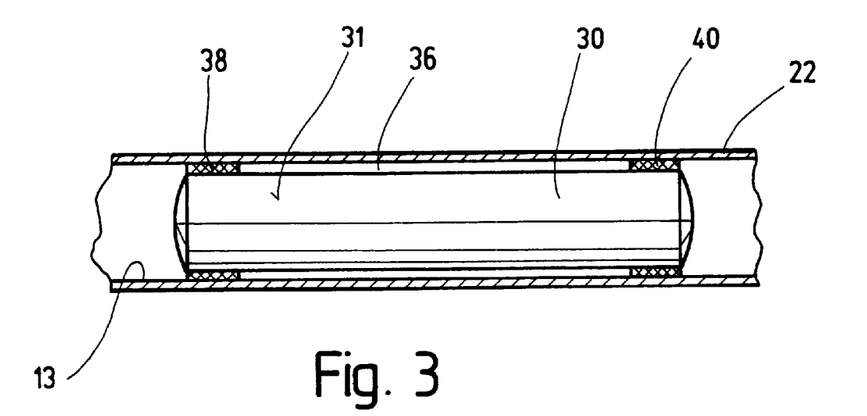
FIG. 3 shows a portion corresponding to that in FIG. 2 of an endoscope according to the present invention, in longitudinal section and in a second embodiment.
Figure 5A:
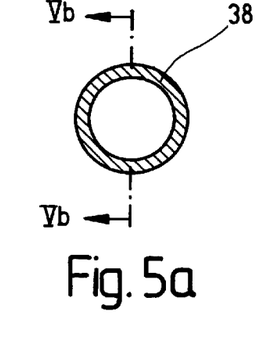
FIG. 5a shows a cross section of a support element in annular form.
Figure 5B:
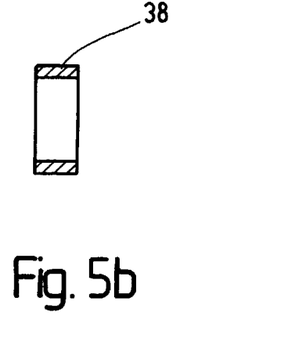

It is apparent from FIG. 3 that it is also possible to mount rod lens 30 using two rings 38 and 40 arranged at its respective end regions (see also FIGS. 5a, 5b). This two-point support on the one hand allows nontilting and axially nondisplaceable immobilization. In this case an air gap 36 is present over a long axial region between outer side 31 of rod lens 30 and inner side 13 of inner tube 22.

Rings 38 and 40, and the further support elements to be described below, are all manufactured from a shrinkable material, and their manner of installation is the same as described previously.

Figure 4:
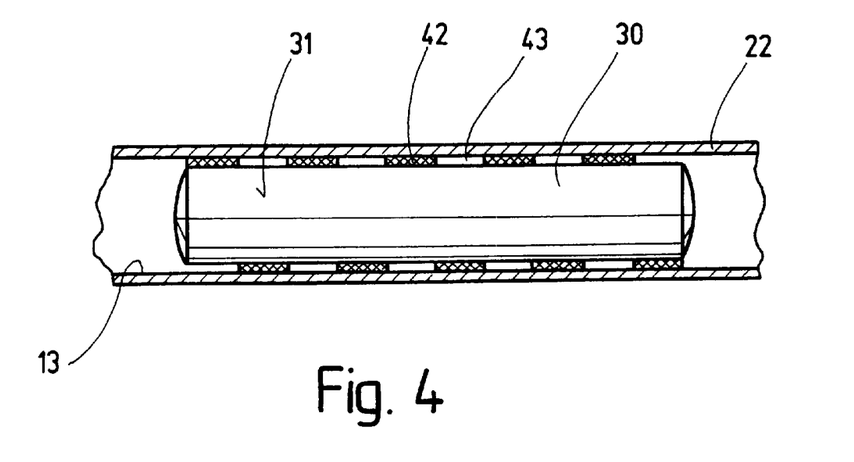
FIG. 4 shows a portion corresponding to that in FIG. 2 of an endoscope according to the present invention, in longitudinal section and in a third embodiment.
Figure 8A:
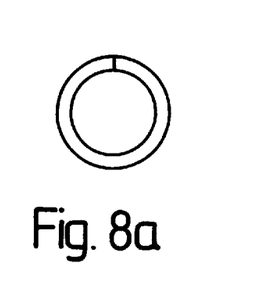
FIG. 8a shows a front view of a support element in the form of a helically wound band.
Figure 8B:
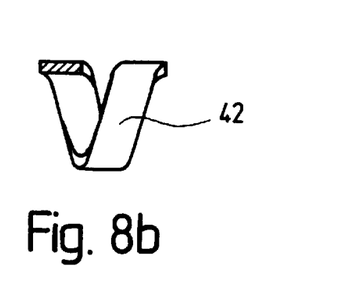

It is evident from FIG. 4, in combination with FIGS. 8a and 8b, that there also exists the possibility of laying the support element, in the form of a helical band 42, around outer side 31 of rod lens 30. This leaves open a continuous helical gap channel 43, so that pressure equalization is possible in the regions on either side of the opposing ends of rod lens 30.

Figure 6A:
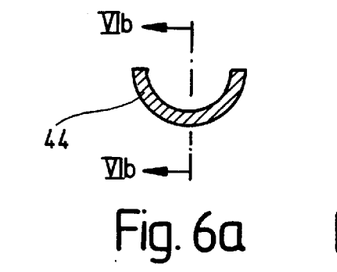
FIG. 6a shows a cross section of a support element in the form of a half-ring.
Figure 6B:
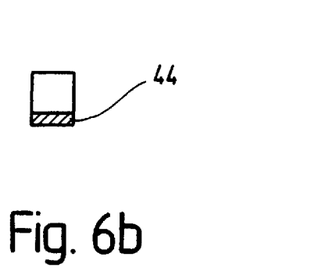
Figure 7A:
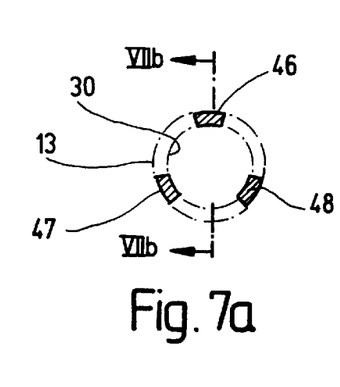
FIG. 7a shows a cross section of support elements in the form of three longitudinal strips.
Figure 7B:
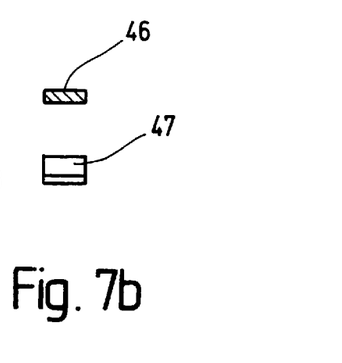

It is evident from FIGS. 6a and 6b that a support element can also be configured in the form of a half-ring 44 or, as is evident from FIGS. 7a and 7b, in the form of several longitudinally extending strips 46, 47, and 48. The two last-named designs again allow sufficient bracing and immobilization simultaneously with pressure equalization or the passage of flushing liquids or the like.

FIGS. 9 through 13 depict several variants of the configuration of the outer side of the lenses and the inner side of the inner tube in order to achieve the additional mechanical interlock mentioned earlier.

Figure 9:
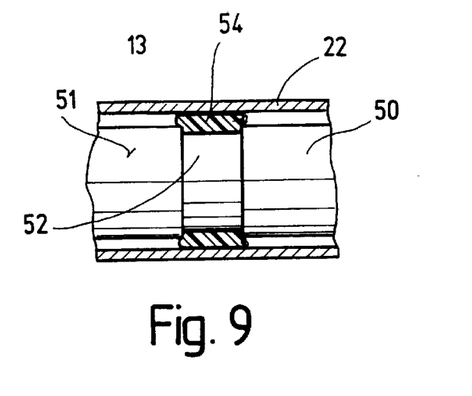
FIGS. 9 through 13 show partial longitudinal sections of various further embodiments of an endoscope according to the present invention.

It is evident from FIG. 9 that rod lens 50, in contrast to rod lens 30, has a groove 52 cut circumferentially into its outer side 51. A support element in the form of a ring 54 has an axial length such that it extends beyond groove 52 on either side. Inner side 13 of inner tube 22 is smooth. Assembly is very simple with this embodiment, since ring 54 merely needs to be slid onto lens 50 until it arrives at its groove 52. After the assemblage has been inserted and the heat treatment has been performed, ring 54 shrinks and presses itself particularly firmly into the annular space between groove 52 and inner side 13 of inner tube 22. This results in a mechanical interlock that inhibits any axial relative movement between ring 54 and lens 50.

Figure 10:
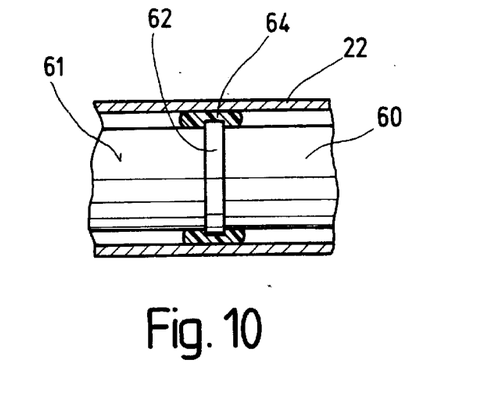

In FIG. 10 an interlock of this kind is achieved by the fact that a circumferential land 62 is provided on an outer side 61 of a rod lens 60. Here again, inner side 13 of inner tube 22 is smooth. Here again, an intensive mechanical interlock occurs between a ring 64 and land 62 after the heat treatment, inhibiting any axial relative displacement between these two components.

Figure 11:
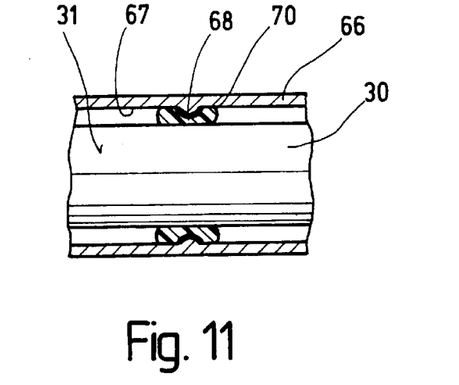

It is evident from FIG. 11 that a radially inwardly projecting annular flange 68 is provided on inner side 67 of inner tube 66. A ring 70 placed around outer side 31 of the smooth rod lens 30 enters into an intimate mechanical interlock with annular flange 68 after the heat treatment. As a result, any relative displacement in the axial direction between ring 70 and inner tube 66 is mechanically inhibited.

Figure 12:
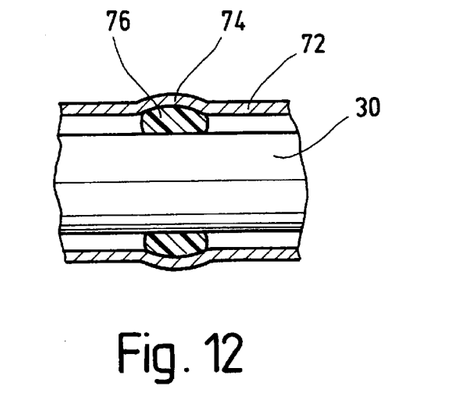

A similar mechanical inhibition is also achieved with the embodiment of FIG. 12. In this case an outwardly oriented protrusion 74 is provided in inner tube 72, into which a ring 76 conformingly fits after the heat treatment. Rod lens 30 having a smooth outer side can again be installed in this case.

Figure 13:
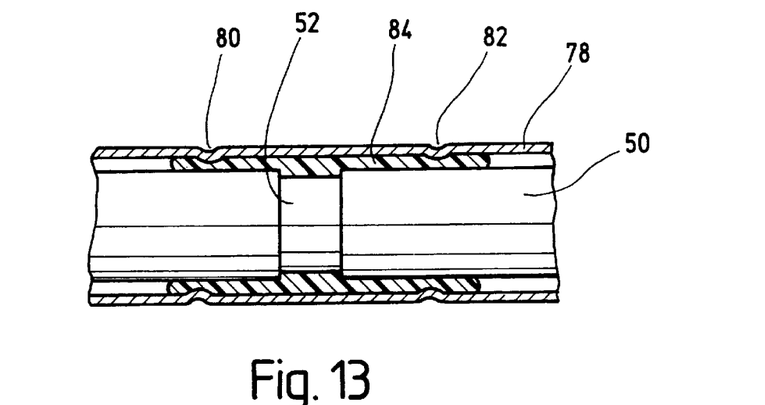

FIG. 13 shows an inner tube 78 in which two beads 80 and 82, axially spaced apart from one another, are provided. Rod lens 50 with the circumferentially cut-in groove 52, already described in conjunction with FIG. 9, is installed in inner tube 78.

To accomplish this, a sleeve element 84 made of the shrinkable material described above, whose axial length is selected so that it axially overlaps both groove 52 and beads 80 and 82, is slid over rod lens 50.

After the heat treatment, an intensive mechanical interlock exists between sleeve element 84 and beads 80 and 82, thus inhibiting any relative displacement in the axial direction between inner tube 78 and sleeve element 84. At the same time, an intimate mechanical interlock has formed between sleeve element 84 and groove 52, thus inhibiting any relative displacement between sleeve element 84 and lens 50. The assemblage or lens 50 is thereby immobilized in particularly secure fashion in its axial position. These multiple interlocking points also make it possible to immobilize endoscopes with a relatively large diameter using relatively thin sleeve elements 84 or relatively thin films.

Figure 14:
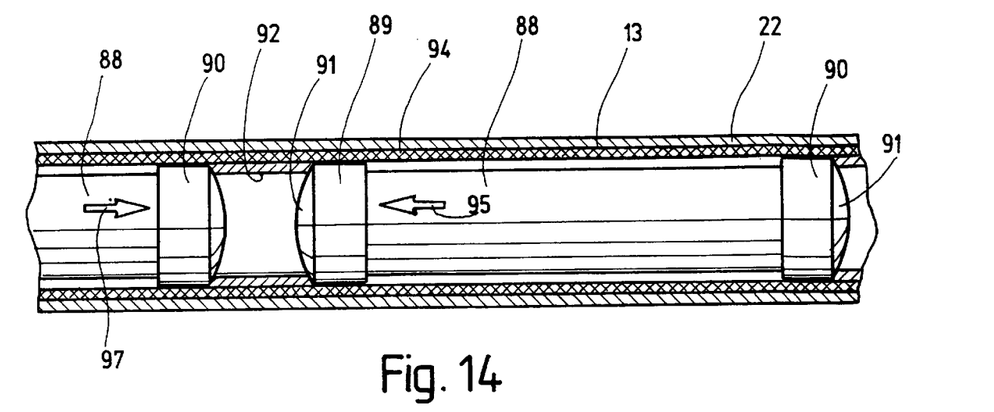
FIG. 14 shows a partial longitudinal section of a further embodiment of an endoscope according to the present invention.

FIG. 14 shows the manner in which multiple dog-bone lenses 88 can be mounted, one behind another, in accordance with the present invention.

Each dog-bone lens 88 has rim cylinders 89 and 90.

Optical surfaces 91 are provided at the ends. A spacer 92 in the form of a tubular segment, which provides axial spacing, is placed between the two dog-bone lenses 88. A support element corresponding to the present invention, in the form of a sleeve 94, is slid over the assemblage of dog-bone lenses 88 and spacer 92, or these elements are slid one by one into the sleeve.

Figure 15:
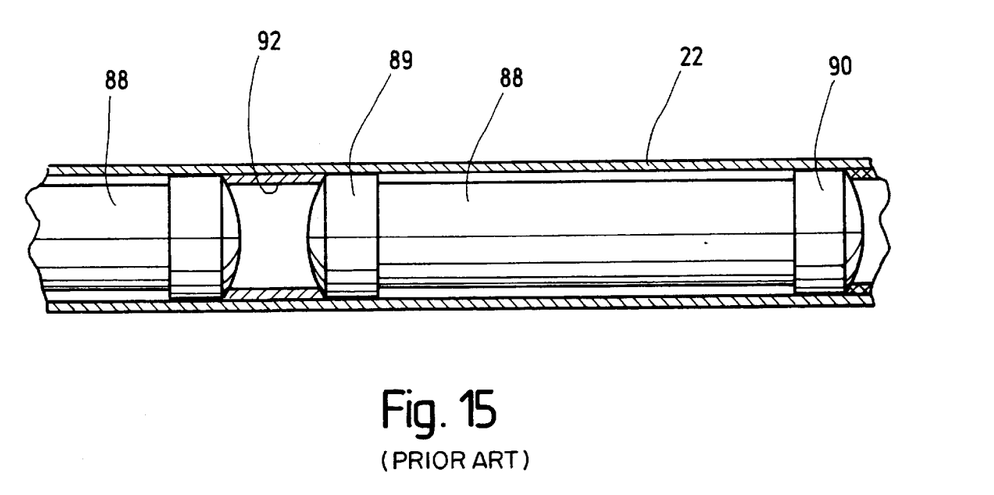
FIG. 15 shows a partial longitudinal section of an endoscope according to the existing art.

Once this assemblage has been slid into, for example, inner tube 22, the shrinkage force results in the further advantage that the two dog-bone lenses 88 are pushed slightly toward one another, as indicated by arrows 95 and 97, so that the relative position is also immobilized under an additional contact pressure. It is evident from FIG. 14 that rim cylinders 89 and 90 are now braced against sleeve 94 and no longer directly on inner side 13 of inner tube 22. If such dog-bone lenses 88 are assembled in the manner that was known from the existing art, as shown in FIG. 15, rim cylinders 89 and 90 come directly into contact with the inner side of inner tube 22, so that forces potentially acting from outside can act directly on the fragile lenses made of glass materials.

To ensure that dog-bone lenses 88 end up located with respect to one another at the desired spacing of the axial length of spacer 92, in the case of assembly according to the existing art it is necessary to apply a corresponding pressure at the proximal and distal ends of the inner tube.

This is now additionally assisted by the shrinkage movement of the film.

What is claimed is:

1. An endoscope having a tubular shaft in whose interior is arranged at least one component of an optical system, and having at least one support element, said at least one support element at least partially surrounds said component and being disposed in a radial gap between an outer side of said component and an inner side of said tubular shaft, wherein said support element is made from a shrinkable material, and wherein, after shrinking of said support element said radial gap is filled up in a manner such that said component is immobilized on said inner side of said tubular shaft via the shrunken support element, and wherein said support element comprises at least one ring.

2. The endoscope of claim 1, wherein said support element comprises a sleeve segment that covers a majority of said outer side of said component.

3. The endoscope of claim 1, wherein said support element comprises two rings that are arranged at opposite ends of said component.

4. The endoscope of claim 1, wherein said outer side of said component is smooth.

5. The endoscope of claim 1, wherein at least one circumferential groove is cut into said outer side of said component, and said support element is arranged in an area having said groove.

6. The endoscope of claim 1, wherein at least one land is provided on said outer side of said component, and said support element is arranged in an area having said land.

7. The endoscope of claim 1, wherein said inner side of said tubular shaft is smooth.

8. The endoscope of claim 1, wherein said inner side of said tubular shaft has at least one groove, and said support element is arranged in an area having said groove.

9. The endoscope of claim 1, wherein said inner side of said tubular shaft has at least one outwardly directed protrusion in a form of a spherical segment, and said support element is arranged in an area having said protrusion.

10. The endoscope of claim 1, wherein at least one annular flange is provided on said inner side of said tubular shaft and said support element is arranged in an area having said annular flange.

11. The endoscope of claim 1, wherein several components are arranged axially one behind another in said interior of said tubular shaft along an axis of said tubular shaft, said support element extends over said several components, and said several components are immobilized with respect to one another in an axial arrangement by that shrunken support element.

12. An endoscope having a tubular shaft in whose interior is arranged at least one component of an optical system, and having at least one support element, said at least one support element at least partially surrounds said component and being disposed in a radial gap between an outer side of said component and an inner side of said tubular shaft, wherein said support element is made from a shrinkable material, and wherein, after shrinking of said support element said radial gap is filled up in a manner such that said component is immobilized on said inner side of said tubular shaft via the shrunken support element, and wherein said support element comprises at least one half-ring.

13. An endoscope having a tubular shaft in whose interior is arranged at least one component of an optical system, and having at least one support element, said at least one support element at least partially surrounds said component and being disposed in a radial gap between an outer side of said component and an inner side of said tubular shaft, wherein said support element is made from a shrinkable material, and wherein, after shrinking of said support element said radial gap is filled up in a manner such that said component is immobilized on said inner side of said tubular shaft via the shrunken support element, and wherein said support element comprises at least two strips that extend in a longitudinal direction of said tubular shaft.

14. An endoscope having a tubular shaft in whose interior is arranged at least one component of an optical system, and having at least one support element, said at least one support element at least partially surrounds said component and being disposed in a radial gap between an outer side of said component and an inner side of said tubular shaft, wherein said support element is made from a shrinkable material, and wherein, after shrinking of said support element said radial gap is filled up in a manner such that said component is immobilized on said inner side of said tubular shaft via the shrunken support element, and wherein said support element comprises a tape wound in helical fashion.

15. A method for mounting components of an optical system in an interior of a tubular shaft of an endoscope, in which at least one support element made of shrinkable material, that at least partially surrounds said component is brought onto an outer side of said component thereby forming an assembly, introducing said assembly into said tubular shaft, and after introduction of said assembly into said tubular shaft, a heat treatment is performed such that said shrinkable material of said support element shrinks, thereby immobilizing said assemblage on an inner side of said tubular shaft, and wherein several components are arranged axially one behind another along an axis of said tubular shaft, and said support element extending over said several components is applied in such a way, that, after said heat treatment, said several components are additionally immobilized relative to one another in their axial arrangement.

* * * * *